United States Patent
Akbari Khorami et al.

(10) Patent No.: US 9,671,378 B2
(45) Date of Patent: Jun. 6, 2017

(54) SENSING DEVICE FOR SPECTROSCOPIC DETECTION OF HYDROGEN PEROXIDE

(71) Applicant: UVic Industry Partnerships Inc., Victoria (CA)

(72) Inventors: Hamed Akbari Khorami, Victoria (CA); Peter Martin Wild, Victoria (CA); Nedjib Djilali, Victoria (CA)

(73) Assignee: UVic Industry Partnerships Inc., Victoria (CA)

( * ) Notice: Subject to any disclaimer, the term of this patent is extended or adjusted under 35 U.S.C. 154(b) by 95 days.

(21) Appl. No.: 14/536,424

(22) Filed: Nov. 7, 2014

(65) Prior Publication Data
US 2016/0131622 A1    May 12, 2016

(51) Int. Cl.
*G01N 33/00*    (2006.01)
*G01N 31/22*    (2006.01)
*G01N 21/77*    (2006.01)

(52) U.S. Cl.
CPC ....... *G01N 31/228* (2013.01); *G01N 21/7703* (2013.01); *G01N 2021/772* (2013.01); *G01N 2021/7773* (2013.01)

(58) Field of Classification Search
None
See application file for complete search history.

(56) References Cited

PUBLICATIONS

Botero-Cadavid et al., "Detection of hydrogen peroxide using an optical fiber-based sensing probe," *Sensors and Actuators B* 185:166-173, 2013.
Del Villar et al., "ESA-Based In-Fiber Nanocavity for Hydrogen-Peroxide Detection," *IEEE Transactions on Nanotechnology* 4(2):187-193, Mar. 2005.
Khorami et al., "Spectroscopic detection of Hydrogen peroxide with an optical fiber probe using chemically deposited Prussian blue," *Electrochimica Acta* 115:416-424, 2014.
Koncki et al., "Optical sensing schemes for Prussian Blue/Prussian White film system," *Analytica Chimica Acta* 424:24-35, 2000.
Koncki, "Chemical Sensors and Biosensors Based on Prussian Blue," *Critical Reviews in Analytical Chemistry* 32(1):79-96, 2002.

*Primary Examiner* — Robert Xu
(74) *Attorney, Agent, or Firm* — Klarquist Sparkman, LLP

(57) ABSTRACT

A sensing device for determining the presence of hydrogen peroxide is disclosed. The sensing device comprises a light guide having a distal portion terminating at a light guide tip and a proximal portion, wherein the light guide tip is proximal to a layer of Prussian blue (PB), which is pure (or essentially free of contaminants). The sensing device produces a fast linear response and is durable, due to the robustness and purity of the PB. The PB is chemically deposited proximal to, or on, the light guide tip using a single-source precursor technique. Methods of making and using the device also are disclosed herein.

8 Claims, 11 Drawing Sheets

SENSING DEVICE FOR SPECTROSCOPIC DETECTION OF HYDROGEN PEROXIDE

FIELD

The subject matter of this application relates to embodiments of a sensing device for determining the presence of hydrogen peroxide, such as by detecting and measuring the concentration of hydrogen peroxide.

BACKGROUND

Hydrogen peroxide ($H_2O_2$) is commonly used in many industrial and medical processes such as water treatment plants and disinfection. It is also a by-product of oxidative metabolisms. Detection and determination of small concentrations of hydrogen peroxide remains a major challenge in many fields where it plays a main role in a variety of damage mechanisms. For example, $H_2O_2$ induces cellular damage in human cells and its presence can be used to diagnose illnesses such as asthma. Hydrogen peroxide is also believed to be responsible for chemical degradation of polymer membranes in Polymer Electrolyte Membrane Fuel Cells (PEM-Fuel cells). Conventional techniques to detect $H_2O_2$ include titrimetric, colorimetric, and gasometric methods, which, in general, require complex equipment and time consuming sample preparation, or have poor selectivity and limits of detection. Electrochemical and spectroscopic techniques, on the other hand, are able to determine small concentrations of $H_2O_2$ and have good selectivity, with spectroscopic techniques being preferred for many biochemical and industrial applications because of their immunity to electromagnetic interference. Spectroscopic detection includes chemiluminescent, fluorescent, and absorptive techniques.

While particular sensors for hydrogen peroxide detection based on the redox reaction of the Prussian blue (PB)-Prussian white (PW) system have been utilized in the field, there are issues associated with such sensors that negatively impact the overall performance of such sensors when applied in various applications.

SUMMARY

Disclosed herein are embodiments of a sensing device for determining the presence of hydrogen peroxide, comprising a light guide having a distal portion terminating at a light guide tip and having a proximal portion, and a sensing component consisting of a layer of Prussian blue situated proximate to the light guide tip. In some embodiments, the sensing device further comprises a light source situated to couple a light beam into the light guide, and a signal processing device coupled to the light guide so as to receive a portion of a light beam reflected from the sensing component. In some embodiments, the light guide can be an optical fiber situated to deliver light from the light source to the sensing component and to deliver reflected light from the sensing component to the signal processing device. Some device embodiments can further comprise a fiber couple, such as a bifurcated fiber situated to deliver a light beam from the light source into the light guide and deliver a portion of the light beam reflected from the sensing component to the signal processing device. The light source can be selected from a white light source, a monochromatic light source, a narrow band light source, or a polychromatic light source further comprising a filter. The signal processing device can be a spectrometer or a light detector.

Also disclosed herein are embodiments of a method for making a sensing device. Some embodiments concern providing a light guide having a distal portion terminating at a light guide tip and a proximal portion; immersing the light guide tip of the distal portion in a single-source precursor and an acidic medium to initiate chemical deposition of a sensing component consisting of a layer of Prussian blue on the light guide tip, wherein the Prussian blue; and annealing the light guide tip at a temperature ranging from 80° C. to 120° C. after the layer of Prussian blue is deposited on the light guide tip. In some embodiments, the method can further comprise preparing the distal portion of the light guide by cleaving an end of the distal portion to form the light guide tip and cleaning the light guide tip with a solvent before chemically depositing the layer of Prussian blue. In some embodiments, the Prussian blue is nanostructured Prussian blue. The single-source precursor can comprise $K_3Fe(CN)_6$ and the acidic medium can be hydrochloric acid. In some embodiments, the Prussian blue is chemically deposited on the light guide tip of the distal portion using light having a wavelength ranging from 380 nm to 800 nm. In yet additional embodiments, the Prussian blue is chemically deposited on the light guide tip of the distal portion at a temperature ranging from 19° C. to 50° C. In other embodiments, the temperature ranges from 35° C. to 45° C. In some embodiments, the light guide tip is annealed at 100° C.

Further disclosed herein are embodiments of a method for determining the presence of hydrogen peroxide, comprising providing a sensing device comprising a light guide having a distal portion terminating at a light guide tip and a proximal portion, wherein the light guide tip is proximal to sensing component comprising a layer of pure Prussian blue (such as Prussian blue that is essentially free of contaminants); and immersing the light guide tip into a solution to determine the presence of $H_2O_2$ in the solution. In some embodiments, the method can further comprise immersing the light guide tip in a solution comprising a reducing agent. The reducing agent is ascorbic acid in some embodiments. In some method embodiments, determining the presence of $H_2O_2$ comprises monitoring the reduction of the Prussian blue to Prussian white. In yet other embodiments, determining the presence of $H_2O_2$ comprises detecting a change in optical properties of the solution resulting from reduction of the Prussian blue to Prussian white. In some embodiments, the method can further comprise quantifying a concentration of hydrogen peroxide present in the solution by detecting changes in reflected light intensity originating from the sensing component.

The foregoing and other objects, features, and advantages of the present disclosure will become more apparent from the following detailed description, which proceeds with reference to the accompanying figures.

BRIEF DESCRIPTION OF THE DRAWINGS

FIG. 5A illustrates results from an embodiment synthesized in the absence of light wherein the reflected light from the light guide tip (PB) is in a wavelength range of 720±15 nm; FIG. 5B illustrates results from an embodiment synthesized using light exposure wherein the reflected light from the light guide tip is in a wavelength range of 720±15 nm; FIG. 5C illustrates results from an embodiment synthesized in the absence of light wherein the reflected light from the light guide tip is in a wavelength range of 420±15 nm; and FIG. 5D illustrates results from an embodiment synthesized using light exposure wherein the reflected light from the light guide tip is in a wavelength range of 420±15 nm.

DETAILED DESCRIPTION

I. Overview and Abbreviations

Figure 1:
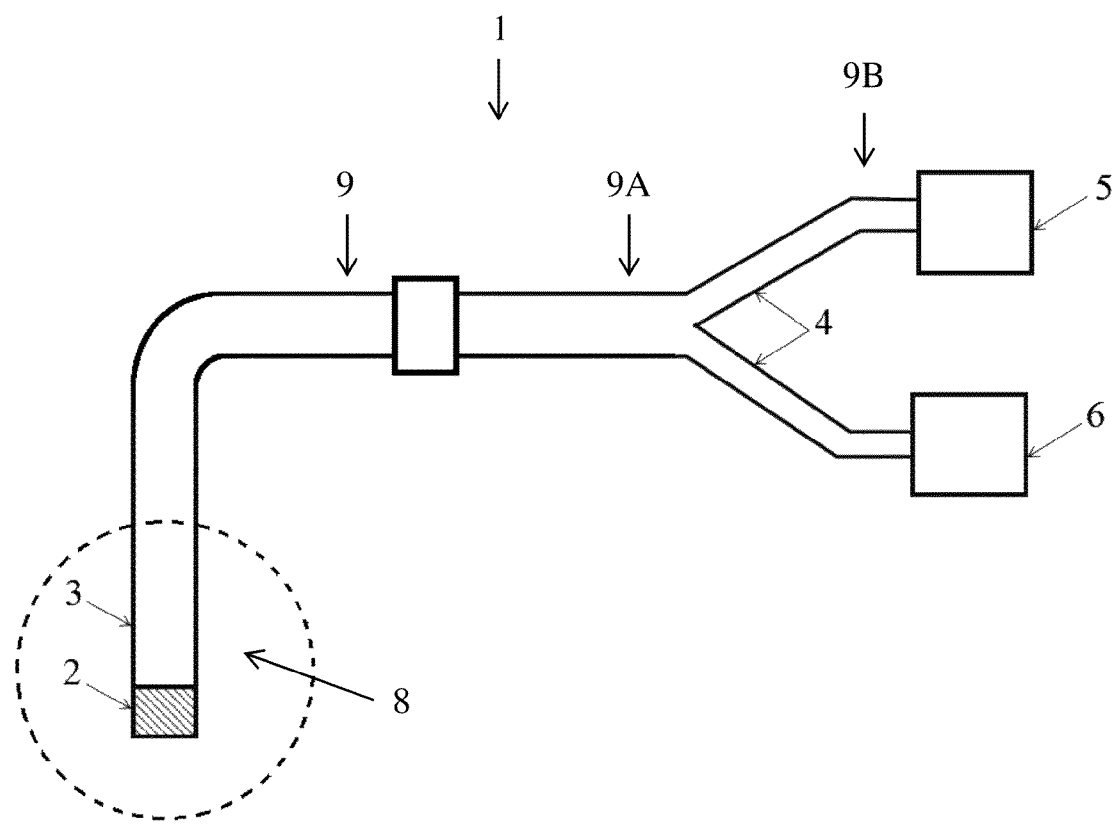
FIG. 1 is a schematic diagram of a sensing device embodiment.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

"PB"=Prussian blue
"PW"=Prussian white
"BG"=Berlin green
"$H_2O_2$"=Hydrogen peroxide II. Introduction While sensors have been developed in the field to detect hydrogen peroxide, there are still issues in the overall performance of such sensors when applied in various applications. The composition of the sensing component of the sensor plays a significant role in the overall performance of a hydrogen peroxide sensor, especially in the aspects of selectivity, sensitivity, and reliability of detection.

In some conventional sensors, a PB film is deposited by employing both a pyrrole benzoic monomer and $Fe^{3+}$ in a reaction mixture to produce a sensing component comprising PB. In such sensors, the final compound produced by the reaction between pyrrole benzoic acid monomers and potassium ferricyanide is a composite of PB and pyrrole benzoic acid polymers (or "polypyrroles"). A drawback of such sensors is that both PB and polypyrrole act as sensing components. Since pyrrole is highly sensitive to reaction with compounds other than hydrogen peroxide, such as ammonia, sensors including the extraneous polypyrroles exhibit poor selectivity towards hydrogen peroxide. Such sensors therefore provide responses that are not as reliable as would be obtained from a sensor having pure PB as the sensing component. A person of ordinary skill in the art would recognize that a practical environment would not, realistically, contain a single compound in isolation; therefore, these conventional sensors do not provide the superior selectivity for a particular target that is exhibited by the sensing devices of the presently disclosed sensing device.

Other conventional sensors utilize PB particles immobilized through a layer-by-layer electrostatic-self-assembly method, in which PB particles are entrapped in a multi-layer structure of polyelectrolytes. Such sensors also exhibit poor selectivity towards hydrogen peroxide because polyelectrolytes also react with compounds other than hydrogen peroxide, which are present in the environment being tested, thereby negatively affecting the response of the sensor. In addition, these types of sensors are only able to detect hydrogen peroxide at a pH that is the same as that of the immobilized multi-layer. For example, a sensor prepared at pH 4 would only detect hydrogen peroxide at pH 4. Thus, the range of applications and/or solutions in which these sensors can be used is limited. Such sensors also suffer from leaching of the multi-layer structure into the sensing test solution containing the hydrogen peroxide. Because of these drawbacks, there is a need for a sensing device with improved selectivity, sensitivity and reliability for determining the presence of hydrogen peroxide, particularly in a liquid phase. Of particular interest is a sensing device comprising a sensing component that is in a pure form and thereby able to achieve better selectivity, sensitivity, and reliability in determining the presence of hydrogen peroxide.

Disclosed herein are embodiments of a sensor device made by depositing a layer of PB in a pure form through a single-source precursor method. "Pure form," as used herein, indicates that the PB is essentially free of contaminants, such as from 99% free to 95% free, or from 99% free to 90% free, or 99% free to 85% free of contaminants. Contaminants can include, but are not limited to, any detectable compounds, ions, or complexes that adversely impact the ability of the device to determine the presence of hydrogen peroxide, such as by reacting with the sensor so as to prevent or substantially prevent the sensor from determining the presence of hydrogen peroxide. In an independent embodiment an exemplary contaminant can be BG. In some embodiments, the PB is nanostructured.

Developing a sensor based on a PB sensing component in a pure form resolves the selectivity issues exhibited by conventional hydrogen peroxide sensors, such as those based on the previously discussed PB/polymers composites, and sensors based on multi-layers of PB and polyelectrolytes. In addition, the disclosed sensing devices exhibit a consistent response in detecting and measuring hydrogen peroxide due to the stable and robust pure PB layer that can be chemically deposited on or proximal to a light guide tip, which is located in the distal portion of a light guide, thereby resolving the leaching problems associated with sensors having a multi-layer structure of PB and polyelectrolytes.

The present disclosure concerns sensing devices for determining the presence of $H_2O_2$. In some embodiments, the sensing device includes a light guide comprising a sensing component, such as PB, which can be deposited onto a tip of the light guide, which is located in a distal portion of the light guide. In some embodiments, the disclosed sensing devices are small in size, flexible, and immune to electromagnetic interference. The prepared sensing devices can be used for developing in-situ sensors for PEM-Fuel cells, as well as portable biosensors.

Also disclosed herein are methods of making and using the sensing devices disclosed herein. In some embodiments, the sensing devices can be used for determining the presence of hydrogen peroxide. In some embodiments, the method comprises detecting hydrogen peroxide using the disclosed sensing device to monitor the redox reaction of PB to PW, also referred to herein as the "Prussian blue-Prussian white system" (or the "PB/PW system"). In some embodiments, the method comprises detecting the associated changes in optical properties of the PB sensing component as it is converted to a Prussian white compound upon reaction with hydrogen peroxide.

The subsequent sections provide details of additional structural features of the sensing devices, methods used to make the sensing components, and methods for determining the presence of hydrogen peroxide, such as by detecting and measuring the concentration of hydrogen peroxide using the sensing devices.

III. Representative Sensing Devices

The sensing devices disclosed herein comprise a light guide having a distal portion and a proximal portion. The distal portion of the light guide can terminate to a light guide tip. The light guide tip can have any suitable geometry, such as flat, curved, square, or round. The light guide can be an optical fiber, a glass rod or other type of light transfer material or component. The light guide can have any length and need not be one unitary piece. For example, in some embodiments, the light guide can comprise various light guide segments that are coupled together.

The proximal portion of the light guide can be connected to a light source and/or a signal processing device. In some embodiments, the proximal end can further be coupled to a fiber couple that connects the light guide to the light source and/or the signal processing device. The fiber couple can be another light guide that may be linear or branched (e.g., bifurcated).

In some embodiments, the light guide tip is associated with the layer of PB. In some embodiments, the light guide tip can be associated with a layer of PB that consists essentially of or consists of PB in a pure form. In embodiments where the layer of PB consists essentially of PB in pure form, the PB is free of any components that materially and adversely affect the performance of the sensing device, such as the contaminants discussed previously. In some embodiments, the PB can be nanostructured. In yet additional embodiments, the layer of PB can be a single layer; that is the layer of PB is not, or is other than, a multi-layer structure of PB.

Figure 2:
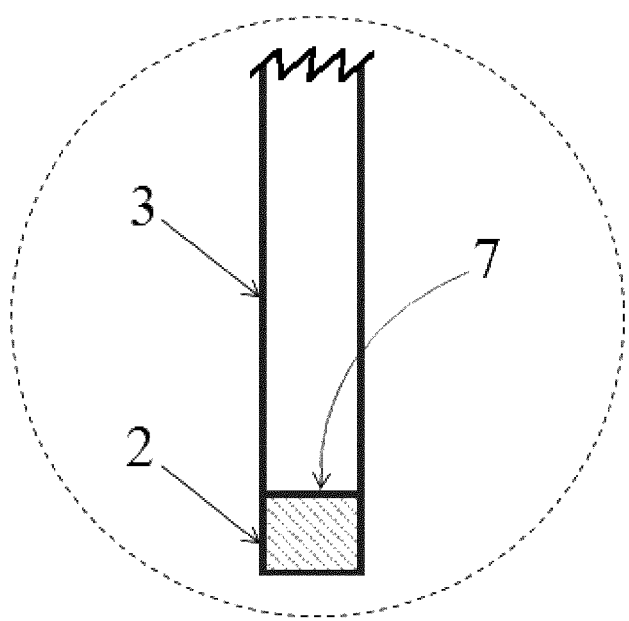
FIG. 2 is a schematic diagram of a distal portion of the sensing device of FIG. 1.

An exemplary embodiment of a sensing device for determining the presence of hydrogen peroxide in a liquid phase is illustrated in FIG. 1 and FIG. 2. According to the embodiment illustrated in FIGS. 1 and 2, the sensing device 1 comprises a light guide 3 and a sensing component 2 located in distal portion 8. The sensing component 2 is located proximal to the light guide 7 tip of light guide 3 located at distal portion 8 of the light guide. A proximal end of light guide 3, which can be any one of positions 9, 9A, or 9B, can be connected to a signal processing device 5 and a light source 6 through a bifurcated light guide 4. In some embodiments, light guide 3 can be an optical fiber of a suitable length that allows the passage of light from the light source 6 to the sensing component 2, and the passage of reflected light from the sensing component 2 to the signal processing device 5. In some embodiments, the sensing component 2 comprises a layer of pure PB. In some embodiments, the PB is chemically deposited on light guide tip 7 of light guide 3 using a single-source precursor approach. In some embodiments, the signal processing device 5 comprises a spectrometer that operates in conjunction with signal processing software. In other embodiments, the signal processing device can be a light detector. In yet other embodiments, visual detection can be used to determine the presence of hydrogen peroxide, such as by observing a color change resulting from the reduction of the Prussian blue sensing component to Prussian white. The light source 6 can be any suitable source of white light, or other electromagnetic radiation. In some embodiments, the light source can be selected from a monochromatic light source, a narrow

IV. Methods of Making and Using the Sensing Device

In some embodiments, PB was selected as an $H_2O_2$ indicator for the disclosed sensing device because of its sensitivity and selectivity toward $H_2O_2$. PB is a ferric ferrocyanide with a basic face-centered-cubic crystalline structure consisting of iron ions linked by the cyanide groups with two chemical forms $Fe_4^{III}[Fe^{II}(CN)_6]_3$ and $KFe^{III}Fe^{II}(CN)_6$. These two chemical forms are commonly known as "insoluble" and "soluble," respectively. Both insoluble and soluble forms of PB are highly insoluble ($K_{sp}=10^{-40}$), the difference between "insoluble" and "soluble" in this context instead refers to the simplicity of potassium peptization. Large metal cations and water molecules, as well as other small molecules like $H_2O_2$, can be accommodated in the open structure of PB. Chemical reduction and oxidation of PB leads to PW (potassium ferrous ferrocyanide) and Berlin green (BG) (ferric ferricyanide), with chemical formula $K_2Fe^{II}Fe^{II}(CN)_6$, and $Fe^{III}Fe^{III}(CN)_6$, respectively.

The $H_2O_2$ detection mechanism in the absorptive technique based on PB relies on the redox reactions of the PB/PW system, and the evaluation of corresponding changes of the optical properties of the sensing component. PB will be reduced to PW in the presence of a strong reducing agent. In particular disclosed embodiments, a strong reducing agent can be an acid that is capable reducing an iron-containing species. In some embodiments, the reducing agent can be selected from ascorbic acid, hydroxylamine, hydroquinone, or a combination thereof. The reverse reaction happens when PW is exposed to a strong oxidizing agent, such as $H_2O_2$, resulting in PB. PB has a strong intervalence charge transfer absorption band near 700 nm (e.g., 720 nm±15) because the transition from $Fe^{III}Fe^{II}$ to $Fe^{II}Fe^{III}$ states absorbs red photons and the red photons are reflected back from the sensing component and transferred from the light guide to the a light detector (e.g., a spectrometer). Other photons not absorbed by the PB can be detected (e.g., visually or using a suitable light detector). In some embodiments, the other photons transmit blue light (e.g., light having a wavelength ranging from 400 nm to 500 nm, such as 420 nm to 480 nm, or 440 nm to 475 nm).

Figure 3:
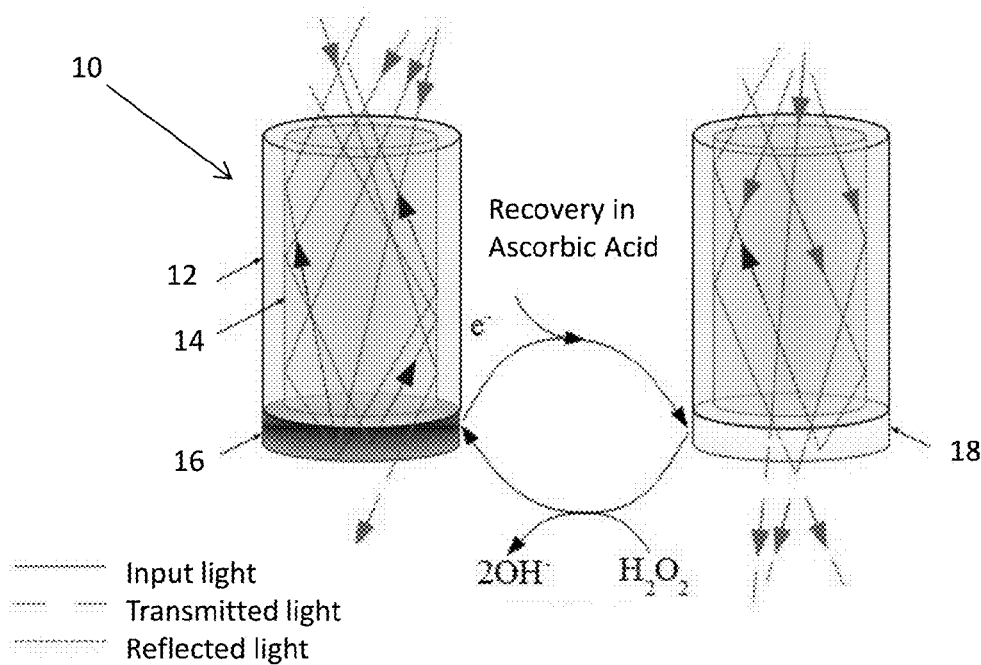
FIG. 3 is a schematic diagram illustrating the detection mechanism of hydrogen peroxide using an exemplary sensing device based on a Prussian blue-Prussian white system.

Accordingly, in some embodiments, propagating electromagnetic radiation having an appreciable absorption by PB can be used. Any wavelength of electromagnetic radiation can be used to interrogate the PB. On the other hand, transparent PW does not have any distinct bands in the visible range of its absorption spectrum. As a result, the increasing absorbance resulting from $H_2O_2$ oxidation of PW to PB can be used to detect the presence of $H_2O_2$. Moreover, the initial PW state can be recovered by exposing PB to ascorbic acid. FIG. 3 illustrates the detection mechanism of $H_2O_2$ using a sensing device based on a chemically deposited PB (16)/PW (18) system onto the tip of an optical fiber light guide 10 having a cladding 12 and core 14.

Generally, PB can be synthesized by electrochemical or chemical methods. In the former case, the substrate onto which the PB is deposited must be electrically conductive. Several chemical methods such as sol-gel, sonochemical, photochemical, hydrothermal, and electrostatic self-assembly have been used to synthesize or immobilize PB nanoparticles and thin films onto non-conductive substrates; however, such techniques do not provide high purity and/or are not efficient or cost-effective.

According to the present disclosure, PB can be chemically deposited to form the sensing component. In some embodiments, the light guide is provided and the light guide tip of the distal portion of the light guide is immersed in a single-source precursor and an acidic medium to initiate chemical deposition of a layer of PB on the light guide tip. In some embodiments, the PB is chemically deposited as a thin film proximal to or associated with the light guide tip of a sensing device through a single-source precursor approach, which is an efficient and cost-effective method for synthesizing PB in pure form. In some embodiments, the PB can be produced as nanoparticles.

In some embodiments, the PB can be chemically deposited at a temperature ranging from 19° C. to 50° C., such as 35° C. to 45° C., with some embodiments using a temperature of 40° C. In some embodiments, the method can also comprise annealing the light guide tip at a temperature ranging from 80° C. to 120° C., such as 100° C., after the layer of Prussian blue is deposited on the light guide tip. Repeatability, durability, and reproducibility of sensor responses were analyzed using multiple sensing devices according to the embodiments disclosed herein. The methods of making the sensing device disclosed herein provide the ability to control particle size, shape, and porosity by tuning synthesis parameters, such as solution pH, concentration of the precursor, temperature, reaction time, and reaction environment conditions (e.g., with light).

In some embodiments, the method of making the sensing device can comprise preparing the distal portion of the light guide by cleaving an end of the distal portion to form the light guide tip and cleaning the light guide tip with a solvent before chemically depositing the layer of Prussian blue. In particular embodiments, the light guide tip is annealed at 100° C. The single-source precursor can comprise $K_3Fe(CN)_6$ and the acidic medium can comprise hydrochloric acid.

In some embodiments, PB and PB films can be synthesized using a solution containing two components, such as an iron (II) salt and hexacyanoferrate (III), or an iron (III) salt and hexacyanoferrate (II). Using these precursors, PB forms directly in the presence of both iron valences. In particular embodiments disclosed herein, hexacyanoferrate (III) can be used as a single-source precursor. In this case, a redox reaction occurs during synthesis to provide both iron valances.

Without being limited to a particular theory of operation, it is currently believed that there are two possible mechanisms for chemical formation of PB from a single source hexacyanoferrate (III). In some embodiments, partial decomposition of hexacyanoferrate (III) can occur in a high acidity environment of a reacting mixture (Equation 1). Free iron (III) cations from the associated complex are reduced to iron (II) cations (Equation 2). The iron (II) cations then react with undissociated hexacyanoferrate (III) anions to form soluble PB (Equation 3). Since the reduction of iron (III) to iron (II) is unfavorable thermodynamically, the driving force can be provided by the reaction of iron (II) cations and hexacyanoferrate (III) anions. The standard free energy change for the combined reactions is −177 kJ mol⁻¹.

$$Fe(CN)_6^{3-}+H^+ \rightarrow Fe^{3+}+6HCN \quad \text{(Equation 1)}$$

$$Fe^{3+}+\tfrac{1}{2}H_2O \rightarrow \tfrac{1}{4}O_2+H^++Fe^{2+} \quad \text{(Equation 2)}$$

$$K^++Fe^{2+}+Fe(CN)_6^{3-} \rightarrow KFe^{III}Fe^{II}(CN)_6 \quad \text{(Equation 3)}$$

In other embodiments, the iron (III) cations produced in Equation 1 and hexacyanoferrate (III) anions present in the solution can form a highly reactive complex of ferric ferricyanide or BG (Equation 4). This mixture has an oxidation potential higher than that of each component, and it even causes oxidation of water. For BG to become PB, the presence of a reducing agent is necessary. It has been reported that BG can oxidize water (solvent), solution impurities, and liberate cyanides through reaction (Equation 5). However, liberated cyanides can play the role of main reducing agent—more than water and the impurities—for the process of PB formation. The reduced BG reacts with free iron (III) cations in the solution and forms insoluble PB (Equation 6).

$$Fe^{3+} + Fe(CN)_6^{3-} \rightarrow Fe^{III}Fe^{III}(CN)_6 \quad \text{(Equation 4)}$$

$$Fe^{III}Fe^{III}(CN)_6 + e^- \rightarrow Fe^{II}Fe^{III}(CN)_6^- \quad \text{(Equation 5)}$$

$$3Fe^{II}Fe^{III}(CN)_6^- + Fe^{3+} \rightarrow Fe_4^{III}[Fe^{II}(CN)_6]_3 \quad \text{(Equation 6)}$$

An investigation has been reported before on the chemical synthesis of PB using hexacyanoferrate (III) and iron (III) chloride. The ratio of the total charges consumed in the reduction of prepared PB and its oxidized form has been studied. Based on this ratio, it was demonstrated that the PB is insoluble, in agreement with the second interpretation.

In some embodiments disclosed herein, PB films were synthesized under two different conditions to determine the effect of light on PB formation: (a) in the presence of light, such as light having a wavelength ranging from 380 nm to 800 nm, and (b) in the absence of light. The reflected light coming from the distal portion of light guide, such as the reflected light originating from the sensing component proximal to the tip of the light guide, during the synthesis process in both conditions can be measured and recorded using the experimental setup described herein. In some embodiments, the reflected light can be light within the visible spectrum, the ultraviolet spectrum, or the near infrared spectrum. In some embodiments, light having a wavelength ranging from 400 nm to 490 nm, such as 440 nm to 490 nm, or 450 nm to 480 nm can be observed when the PB is interrogated with light through the light guide. In some embodiments, the PB can absorb light at a wavelength ranging from 680 nm to 730 nm, such as 700 nm to 730 nm, or 710 nm to 720 nm. Simultaneously, a microscopic glass slide can be dipped into the reaction mixture to prepare a sample for investigation using Raman spectroscopy of the compounds produced under each set of conditions.

Figure 4:
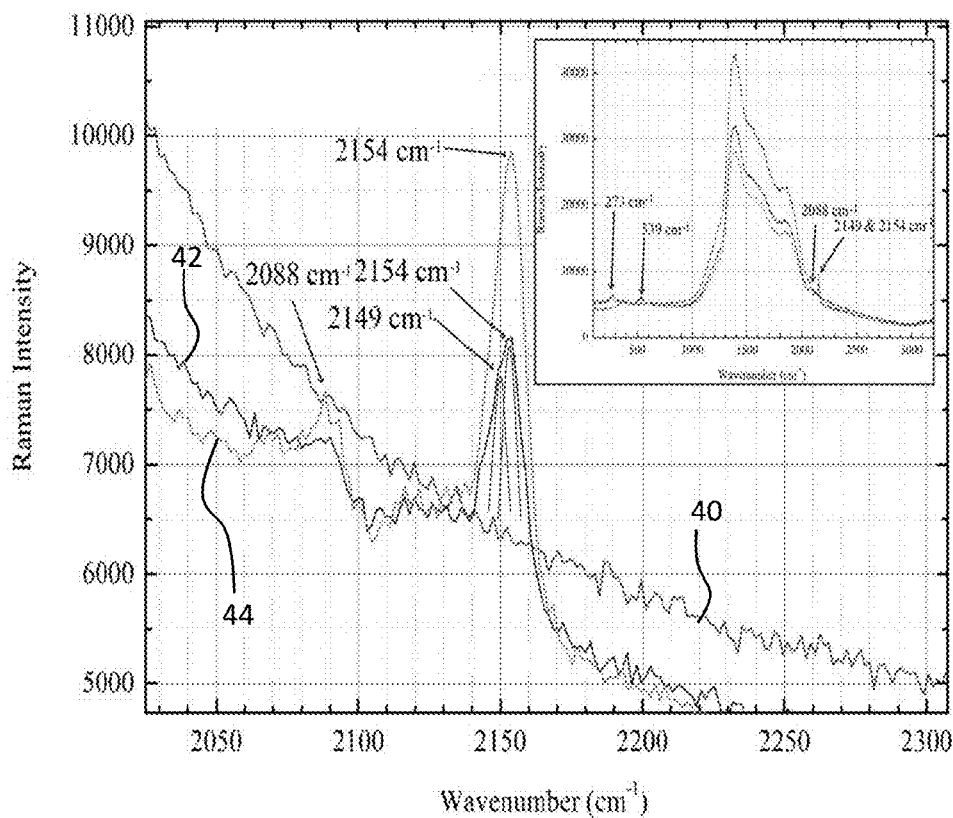
FIG. 4 is a combined Raman spectrum taken in the range of 2025-3010 cm$^{-1}$ illustrating results obtained from an uncoated glass substrate (40); a Prussian blue sample synthesized in the absence of light (42), and a Prussian blue sample synthesized under fluorescent lamp light exposure (44); the inset provides an zoomed view of the Raman spectra of the same samples in the range of 100-3200 cm$^{-1}$.

FIG. 4 shows the Raman spectra of exemplary samples synthesized with light, in the absence of light, as well as a control uncoated glass substrate in the range of 2025 to 3010 cm$^{-1}$. The inset in FIG. 4 shows the spectra of the same samples in the range 100 to 3200 cm$^{-1}$. In the inset of FIG. 4, the broad peaks in the range of 1000 to 2300 cm$^{-1}$ correspond to the fluorescence spectra of glass substrate. The peaks at 273 and 539 cm$^{-1}$ correspond to iron-cyanide bending vibration modes, and the peaks at 2088, 2149, and 2154 cm$^{-1}$ correspond to cyanide vibration modes. In FIG. 4, the spectrum of the sample synthesized with light has a weak peak at 2088 cm$^{-1}$ and a very strong peak at 2154 cm$^{-1}$. In contrast, the spectrum of the sample synthesized in the absence of light has a very weak peak at 2088 cm$^{-1}$ and a strong peak consisting of two maxima at 2149 and 2154 cm$^{-1}$.

The weak peak around 2088 and very strong peak at 2154 cm$^{-1}$ are the characteristic peaks for PB. As shown in FIG. 4 the sample synthesized using light has the same characteristic peaks, and since it does not exhibit any extra peaks, it is therefore pure PB. The strong peak at 2149 cm$^{-1}$ is the characteristic peak for BG. The sample synthesized in the absence of light has a strong peak at 2149 cm$^{-1}$, which indicates the presence of BG in the sample. It also has a very weak peak around 2088 cm$^{-1}$ and a distinct peak at 2154 cm$^{-1}$, which are the characteristic peaks of PB. Therefore, the sample synthesized in the absence of light likely has both PB and BG in the form of $\{Fe_4^{III}[Fe^{II}(CN)_6]_3\}_x\{Fe^{III}Fe^{III}(CN)_6\}_{1-x}$.

These results establish that iron (III) is reduced to iron (II) even in the absence of light. In some embodiments, the iron (II) production rate is not sufficient to form just PB, and another reaction occurs between iron (III) and hexacyanoferrate (III) to form BG. In other embodiments, exposure to light during the synthesis of PB can promote the reduction of iron (III) to iron (II) at a rate that is sufficiently high to form pure PB.

FIGS. 5A-5D illustrate the intensity of reflected light coming from the distal end of a light guide during the synthesis process. The intensities integrated over the range of 720±15 nm and 420±15 nm are shown respectively in FIGS. 5A and 5B, and FIGS. 5C and 5D. FIGS. 5A and 5C and FIGS. 5B and 5D illustrate results obtained from samples synthesized in the absence of light and under light, respectively.

In general, two phenomena can affect the amount of light reflection from the sensing component of the sensing device, namely (1) changes in the reaction mixture that generally result in changes in the imaginary part of the reaction mixture's refractive index; and (2) variation in the precipitation of the sensing component onto the light guide tip of the light guide, with each of PB and PW having its own characteristic absorbance spectrum.

Figure 5A:
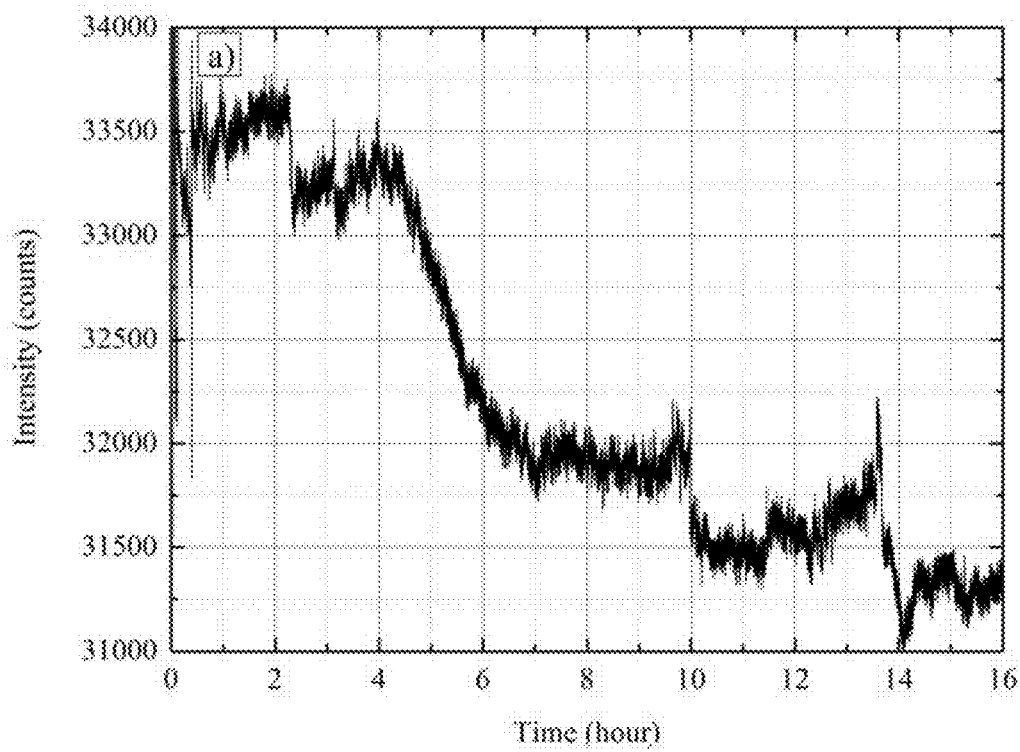
FIGS. 5A-5D depict light reflection from the distal portion of a light guide during synthesis under particular reaction conditions.
Figure 5B:
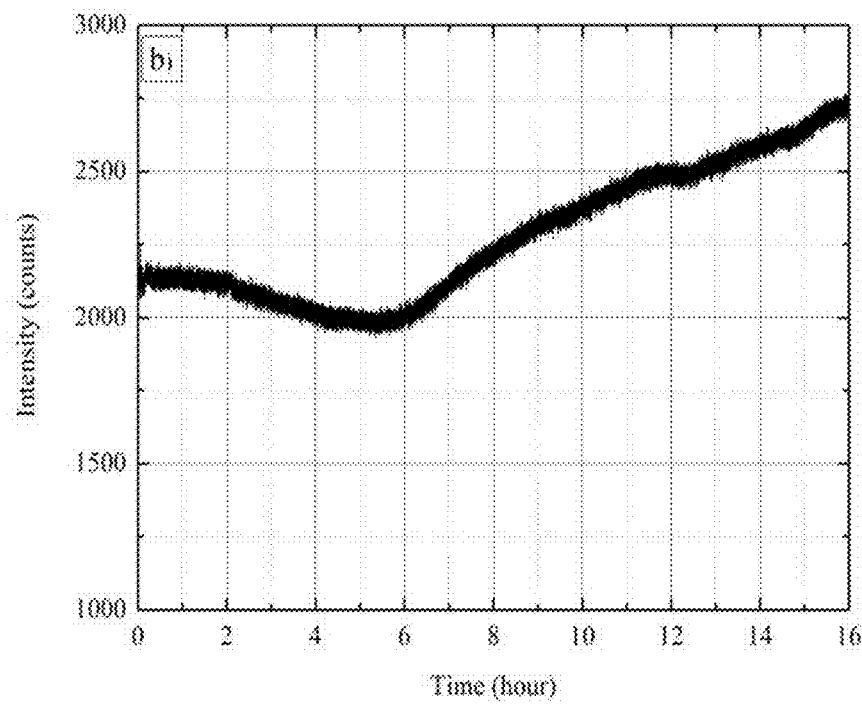
Figure 5C:
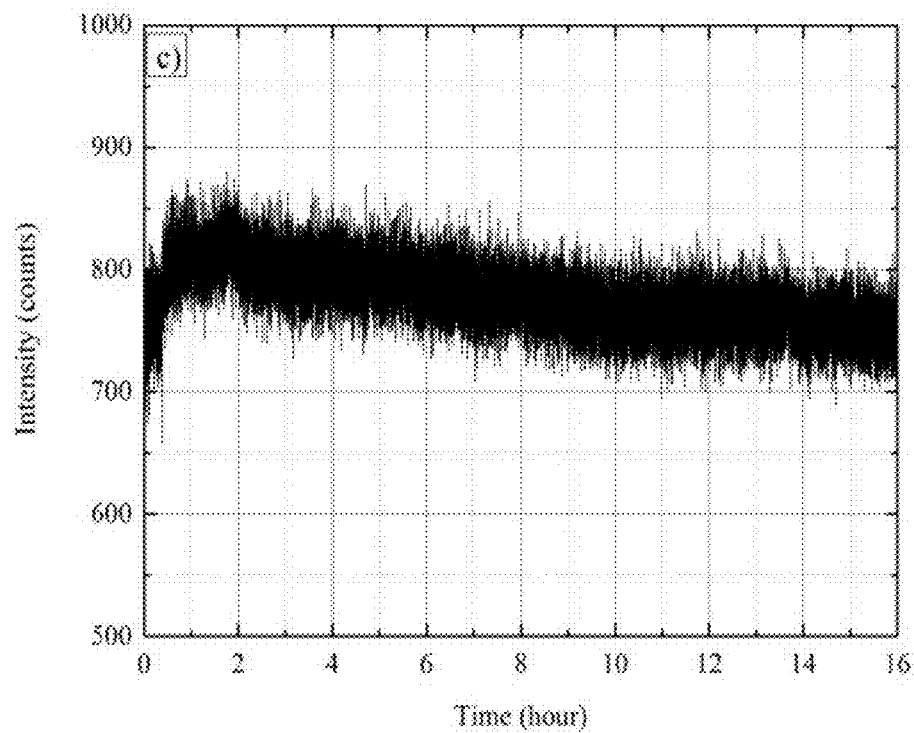
Figure 5D:
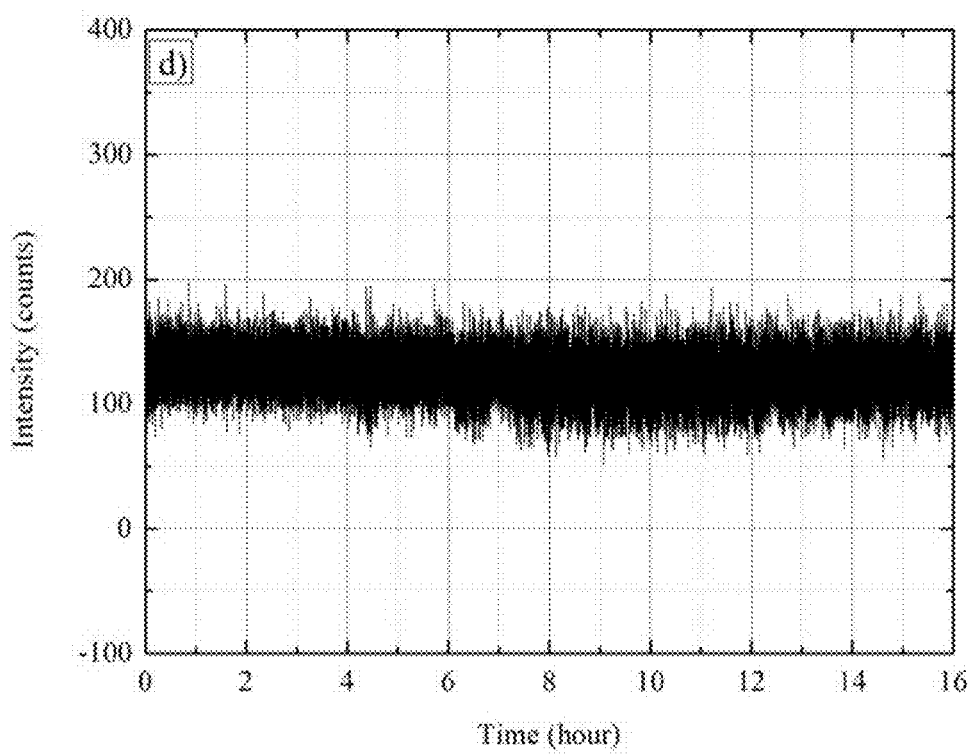

As illustrated in FIG. 5A, the intensity of light around 720 nm decreases during synthesis in the absence of light. Without being limited to a particular theory, it is currently believed that this may happen when no PB is being produced, or when PB is produced but its formation rate is very low. Traces of PB can be seen in the Raman spectrum for the sample synthesized in the absence of light. Therefore, PB can be produced in the absence of light; however, the effect of changes of reaction mixture's refractive index can dominate and cause a decrease in light reflection from the sensing component. FIG. 5C illustrates the intensity of light around 420 nm for a sample synthesized in the absence of light, which initially increases, and starts to decrease after an hour. Increasing the intensity at this wavelength can evidence the formation of BG and it shows that BG can begin to form as soon as the light guide tip of the light guide is introduced into the reaction mixture in the absence of light. The decrease of intensity after the initial period likely is due to the change in the reaction mixture's refractive index in the light, with reflection becoming dominant. The increase of light reflection produced by absorbance around 720 nm for the sample synthesized using light illustrates the high rate of PB formation in this condition (FIG. 5B). The purity of synthesized PB under the light is supported by the absence of change in the light reflection around 420 nm (FIG. 5D).

In particular embodiments, the results of monitoring the light reflection from the distal portion of light guide during the synthesis in the absence of light and under the light are in good agreement with Raman spectra of the synthesized samples. Both imply the formation of pure PB while the synthesis is being done under the light, and formation of PB and BG simultaneously while the synthesis is being done in the absence of light.

Figure 6:
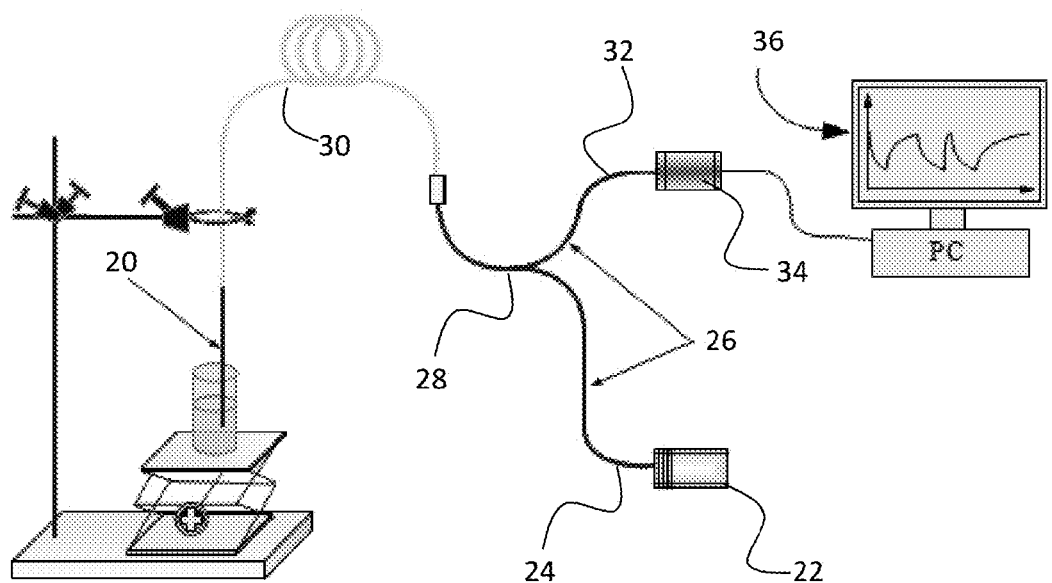
FIG. 6 illustrates an exemplary setup for measuring reflected light using a representative sensing device, wherein the reflected light is associated with the reduction of the PB proximal to the light guide tip to Prussian white (PW).

FIG. 6 illustrates an exemplary setup for using the sensing device disclosed herein. As illustrated in FIG. 6, this exemplary setup can be used to measure the reflected light coming from the PB/PW system deposited proximal to, or on the light guide tip located in the distal portion of the light guide 20. The light generated by a white light source 22 is carried along a first arm 24 of a fiber couple, such as bifurcated optical fiber 26 and through a common arm 28 of the bifurcated optical fiber, reaching the sensing component on the light guide tip of the light guide 20, which is connected to the common arm 28 through optical fiber 30 having a suitable length. At least part of the scattered light from this sensing component is collected by the light guide 20 and guided back through the common arm 28 and a second arm 32 of the bifurcated optical fiber 26 into a spectrometer 34, which measures the intensity of the light. The reflected spectrum can be analyzed using suitable software 36. In particular disclosed embodiments, the integrated values of intensity over the full range of the spectrometer can be evaluated to determine the response of the PB/PW system during both the oxidizing and the reducing steps. The sensing devices can be used to determine the presence of hydrogen peroxide, such as by detecting hydrogen peroxide in an environment (e.g., in solution). The hydrogen peroxide can be detected by monitoring the reduction of PB to PW, as discussed herein. In some embodiments, determining the presence of $H_2O_2$ comprises detecting a change in optical properties of the solution resulting from reduction of the Prussian blue to Prussian white, such as the intensity of light reflected by the PB. In some embodiments, the concentration of hydrogen peroxide that is present in a sample can be quantified by detecting changes in reflected light intensity originating from sensing component.

In particular embodiments, an optical fiber light guide is described for the detection and measurement of small concentrations of $H_2O_2$ in liquid phase. A sensing component comprising PB serves as an indicator of $H_2O_2$ in a spectroscopic manner. A pure and robust PB film can be deposited proximal to or onto the tip of the optical fiber through a simple chemical method using the single-source precursor, potassium ferricyanide. In some embodiments, the effect of light exposure during methods of making the sensing devices can indicate that light exposure during synthesis can lead to formation of pure PB film, while synthesis in the absence of light can lead to co-precipitation of PB and BG.

In particular embodiments, the intensity response of the sensing devices disclosed herein follows an inverse exponential behavior which is in accordance with the physics of diffusion. The characteristic time taken from the inverse exponential equation, which is the ≈63% of the time for intensity to reach the saturation level, shows a linear relationship with the $H_2O_2$ concentration in a log-log scale.

Several sensing methods with different sequences of $H_2O_2$ concentrations and multiple light guide embodiments fabricated using methods disclosed herein demonstrate the repeatability, reliability, and reproducibility of the sensing devices. The durability of the sensing devices also can be confirmed by comparing the sensing behaviors of the sensing devices after being made, with particular embodiments maintaining durability for several months, such as four to seven months after fabrication. In some embodiments, the sensing behavior of the sensing devices remains unchanged, but a small increase in response time can occur over the lifetime of the sensing devices; however, this can be addressed by a periodic recalibration of the sensing device.

The sensing devices demonstrated disclosed herein include features that contribute to their practical and efficient use, such as small size, flexibility, and immunity to electromagnetic interference combined with the sensing properties of the synthesized PB, and in particular high sensitivity and selectivity towards $H_2O_2$, the disclosed sensing component and sensing device provide high performance, portable $H_2O_2$ sensing devices applicable for in situ measurements in polymer electrolyte membrane fuel cells, as well as in minimally invasive biosensors.

V. Examples

Materials

Potassium hexacyanoferrate (III) (product No. 13746-66-2) from Sigma-Aldrich was used as single-source precursor in an aqueous solution of hydrochloric acid (HCl) (37%) for synthesizing PB onto the tip of an optical fiber. L-ascorbic acid from Aldrich (catalog No. 25,556-4), was used as the reducing agent for the PB to PW reaction. Glacial acetic acid, (product No. 00598-468) from Anachemia and sodium acetate trihydrate (product No. S-1850) from ACP Chemicals were used to prepare an acetate buffer solution (ABS) at pH 4.0 in which the $H_2O_2$ solutions and ascorbic acid were prepared. The reducing solution was prepared in ABS with 0.04 mol $L^{-1}$ of L-ascorbic acid. $H_2O_2$ (30 wt %) from ACP Chemicals and used to prepare the oxidizing solutions at different concentrations in ABS. Sodium hydroxide (NaOH) and hydrochloric acid (HCl) at concentrations of 0.1 mol $L^{-1}$ were used to adjust the pH of the solutions to the desired values. All chemicals were used as received with no further purification. The water used in the experiments was purified with a four-cartridge purification system (Super-Q Plus, Millipore, Billerica, Mass.) and had a resistivity of 18.2 MΩ cm. The optical fiber was a multi-mode AFS50/125Y from Thorlabs (Newton, N.J.), with core and cladding diameters of 50 μm and 125 μm, respectively.

Chemical Deposition of PB

In this example, the PB film was deposited chemically using the distal portion of an optical fiber as a substrate. The optical fiber was cleaved and cleansed with isopropanol. In a synthesis process, 0.25 mmol of $K_3Fe(CN)_6$ was added to 25 mL of an aqueous solution of 0.1 mol $L^{-1}$ hydrochloric acid. The optical fiber was immersed in this prepared mix, and was maintained at 40° C. under continuous stifling at 300 rpm for 10 hours. The synthesis process was done under fluorescent lamp light exposure. Finally, the optical fiber was left inside the solution, which was allowed to cool to room temperature. The prepared sensing device was removed from the solution and left at room temperature and relative humidity for one day, and then it was annealed at 100° C. for 15 minutes.

In some embodiments, PB films were synthesized in two conditions to determine the effect of light on PB formation: (a) under light, and (b) in the absence of light. The reflected light coming from the distal portion of optical fiber during the synthesis process in both conditions was measured and recorded using the experimental setup shown in FIG. 6. Simultaneously, a microscopic glass slide was dipped into the reaction mixture to prepare a sample for investigation the Raman spectra of produced compounds in each condition. The results from this example are illustrated in FIGS. 4 and 5A-5D.

The results of monitoring the light reflection from the distal portion of optical fiber during the synthesis in the absence of light and under the light were in good agreement with Raman spectra of the synthesized samples. Both imply the formation of pure PB while the synthesis is being done under the light, and formation of PB and BG simultaneously while the synthesis is being done in the absence of light.

Characterization of the PB

In this example, the effect of light exposure in the synthesis process was characterized by Raman spectroscopy. Two samples were prepared on plain microscope slides using two different conditions: (1) preparation under fluorescent lamp light exposure, and (b) preparation in the absence of light. The Raman spectra were recorded using Renishaw inVia microRaman system equipped with a He—Ne laser source with excitation at 785 nm and a laser power of 1 mW. The light reflection from the distal portion of optical fibers during synthesis in both conditions was recorded and analyzed.

Sensing Test Procedures and Instrumentation

In this example, the sensing behavior of the sensing device to solutions with concentrations of $H_2O_2$ ranging from 2 µmol $L^{-1}$ to 400 µmol $L^{-1}$ was evaluated in the liquid phase. $H_2O_2$ solutions were prepared in ABS with a pH of 4.0±0.1. L-ascorbic acid in solution was used as a reducing agent in all tests. This solution was prepared at a concentration of 0.04 mol $L^{-1}$ using ABS as a solvent and adjusting its pH to 4.0±0.1. The pH measurements of all the prepared solutions were obtained using a digital pH-meter (AR25 Accumet®, Fisher Scientific, Hampton, N.H.) and an (Ag|AgCl) electrode.

The sensing measurement methods disclosed herein included immersing the distal portion of the light guide in the ascorbic acid and $H_2O_2$ solutions alternately for the recovery and oxidation steps of the PB/PW system. Three sequences of concentrations of $H_2O_2$ solutions were used during the tests. In the first, $H_2O_2$ concentrations were chosen randomly in the range of 2 µmol $L^{-1}$ to 400 µmol $L^{-1}$. In the second, the concentration of $H_2O_2$ was increased from 2 µmol $L^{-1}$ to 200 µmol $L^{-1}$ and then decreased back to 2 µmol $L^{-1}$. In the final sequence, $H_2O_2$ concentrations were decreased from 400 µmol $L^{-1}$ to 5 µmol $L^{-1}$ and increased back to 400 µmol $L^{-1}$.

In each of the sequences, the distal portion of the light guide was initially immersed in an ascorbic acid solution to promote the reduction of PB to PW. When the intensity of reflected light from the light guide plateaued to a minimum level, it was considered to have reached the PW state. The optical fiber was then removed from the ascorbic acid and placed in the $H_2O_2$ solution and kept there until the intensity plateaued to a maximum, indicating the oxidation from PW to PB.

In this particular example, the exemplary setup illustrated in FIG. 6 was used for the measurements of the reflected light coming from the PB/PW system deposited on the distal portion of the optical fiber. The light generated by a white light source (LS-1, OceanOptics, Dunedin, Fla.), was carried along the arm 1 of a fiber couple, such as a bifurcated optical fiber (BIF200-UV-Vis, OceanOptics) and through the common arm of the bifurcated optical fiber, reaching the sensing component on the light guide tip of the distal portion of the light guide connected to the common arm. Part of the scattered light from this sensing film of PB/PW was collected by the optical fiber and guided back through the common arm and arm 2 of the bifurcated optical fiber into an optical fiber spectrometer (USB2000, OceanOptics), which measured the intensity of the light in a wavelength range of 370 to 1048 nm. The reflected spectrum was sampled at a frequency rate of 1 Hz using the software SpectraSuite (OceanOptics, Dunedin, Fla.). The integrated values of intensity over the full range of the spectrometer (i.e. 370 to 1048 nm) were evaluated to study the response of the PB/PW system during both the oxidizing and the reducing steps.

Sensing Behavior

Figure 7:
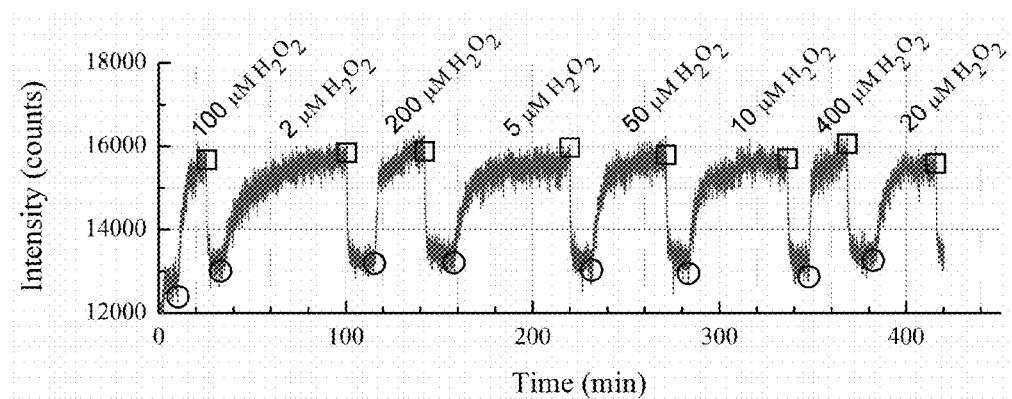
FIG. 7 is a graph of intensity (counts) versus time (minutes) illustrating the intensity response of a sensing device such as illustrated in FIG. 1 to immersion in solutions with random hydrogen peroxide concentration.

The time response of the intensity of the reflected light from the light guide tip of the distal portion of the light guide during its immersion in solutions at random concentrations of $H_2O_2$ is shown in FIG. 7. The circles and squares indicate the instant at which the distal portion of the light guide was immersed into the $H_2O_2$ test solution and ascorbic acid, respectively. Since PW has a low absorbance under visible light, when the film is in PW state the majority of the light transmits through the film, and consequently, a lower intensity of reflected light is attained. The intensity of the recorded light starts rising after the immersion of the distal portion of the light guide in the $H_2O_2$ solutions due to oxidation of PW to PB. This behavior continues until plateauing at a maximum reflectance in PB state. Following the immersion of the distal portion of the light guide in ascorbic acid, the intensity decreases as the reagent returns the PB deposited film to its PW state.

The intensities after each immersion shown in FIG. 7 reach essentially the same value. The changes in the intensity of the reflected light from the PB/PW system are related to the total amount of $H_2O_2$ that enters in contact with the sensing film and the extent of the reaction. In addition, the porosity and particle size of the PB/PW structure determine the surface area of the film accessible to $H_2O_2$. These parameters control the extension of the reaction between the $H_2O_2$ and sensing film. As a result, the intensity of the optical signal is related to the extent of reaction and not to the concentration of the $H_2O_2$. In the case of the sensing devices disclosed herein, only the portion of the sensing film that covers the flat portion of the distal portion is responsible for the light scattered back into the optical fiber and that is measured by the spectrometer. Due to the small amount of PB/PW compound involved in the reaction and the constant intensity after each test performed, it is currently believed that the test solutions are able to oxidize almost all the PW to PB even at very low concentrations of $H_2O_2$, which directly affects the detection limit of the sensing device. Regardless, there is a beneficial distinction between the signals corresponding to the tests at different concentrations of $H_2O_2$. The time it takes the signal to reach the saturation level decreases with increasing concentrations of $H_2O_2$. This behavior is governed by the increased diffusion rates associated with the higher concentration potentials.

Figure 8:
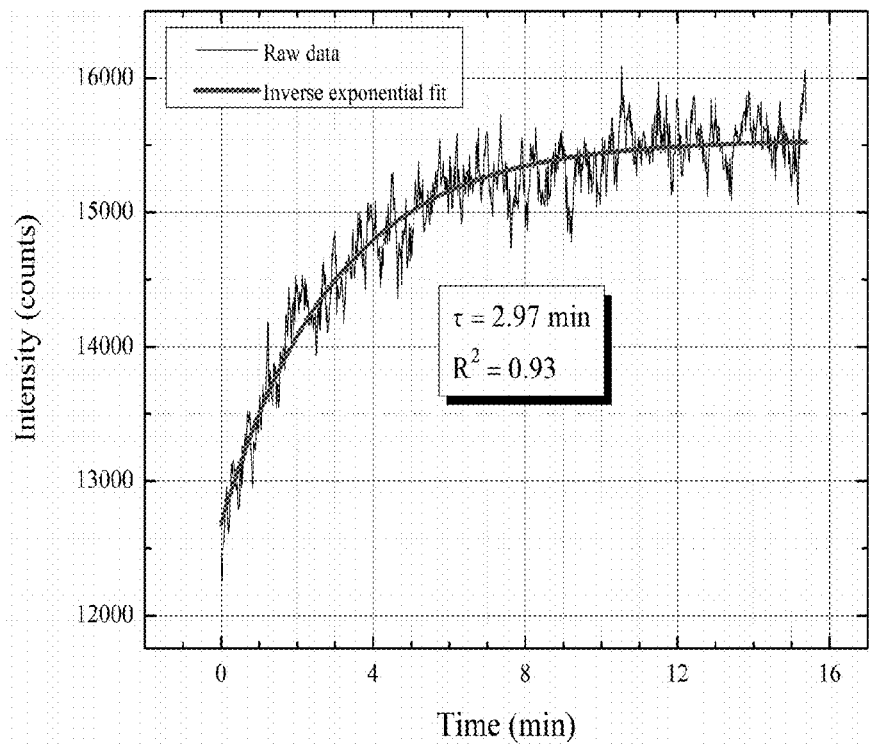
FIG. 8 is a graph of intensity (counts) versus time (minutes) illustrating the intensity response of a representative sensing device and an inverse exponential fit to immersion in 100 µM hydrogen peroxide solution.

In this example, the intensity response of each individual test was brought to the origin of the time axis at the moment of immersion in each $H_2O_2$ solution, and an inverse exponential curve was fitted to it. All responses fitted well to the following equation:

$$I(t) = I_0 + A\left[1 - \exp\left(-\frac{t}{\tau}\right)\right] \quad \text{(Equation 7)}$$

wherein I(t) is the intensity at the time t; $I_0$ is the intensity level while the sensing device was immersed into the $H_2O_2$ solutions; τ is the time elapsed for the signal to reach (1-1/e) equal to 63% of the intensity at saturation and was the parameter used to evaluate the time response of the sensing device; and A is a constant that related to the geometry of the film, the diffusion conditions through the PB structure, and the oxidation of PW to PB. This inverse exponential behavior is consistent with the diffusion mechanism underlying the operating principle of the sensing device. FIG. 8 shows the response of the light guide when its distal portion was immersed in 100 μM of $H_2O_2$ solution.

Figure 9:
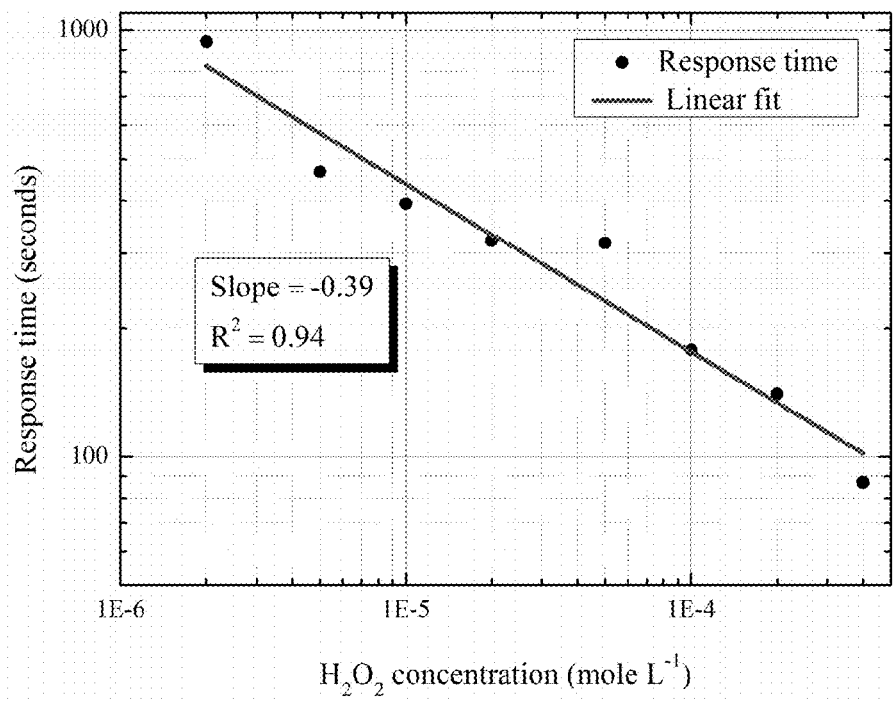
FIG. 9 is a graph of response time (seconds) versus $H_2O_2$ concentration (mol/L) illustrating the time response of a representative sensing device as a function of hydrogen peroxide concentration.

The characteristic response time, τ, versus the $H_2O_2$ concentration on a log-log scale is plotted in FIG. 9. The sensing devices exhibit a linear response to $H_2O_2$ concentration on a log-log scale.

One of the features of the sensing devices disclosed herein that distinguish them from conventional sensors is the nearly-constant signal baselines in the response at either the PB or the PW state, such as those illustrated in FIG. 7. As previously discussed, conventional fiber-sensors based on the PB/PW system are fabricated by immobilizing PB using the electrostatic self-assembly of polyelectrolytes. Reported baselines of such probes were not stable, suggesting that not all the immobilized PB/PW takes part in the redox reactions. This causes uncertainty in the interpretation of the behavior of the conventional probes. An additional advantage of the pure chemical deposition method used here is the faster response and recovery times, which can be attributed to the easier diffusion in a pure PB/PW, as opposed to the slower diffusion through a multilayered structure of polyelectrolytes.

The uncertainties in determining concentration and response time of the sensing device were estimated for 100 μM $H_2O_2$ since it is a representative value of the evaluated range. The uncertainties for this case are ±5% for the concentration and ±14% for the response time.

Repeatability

Figure 10:
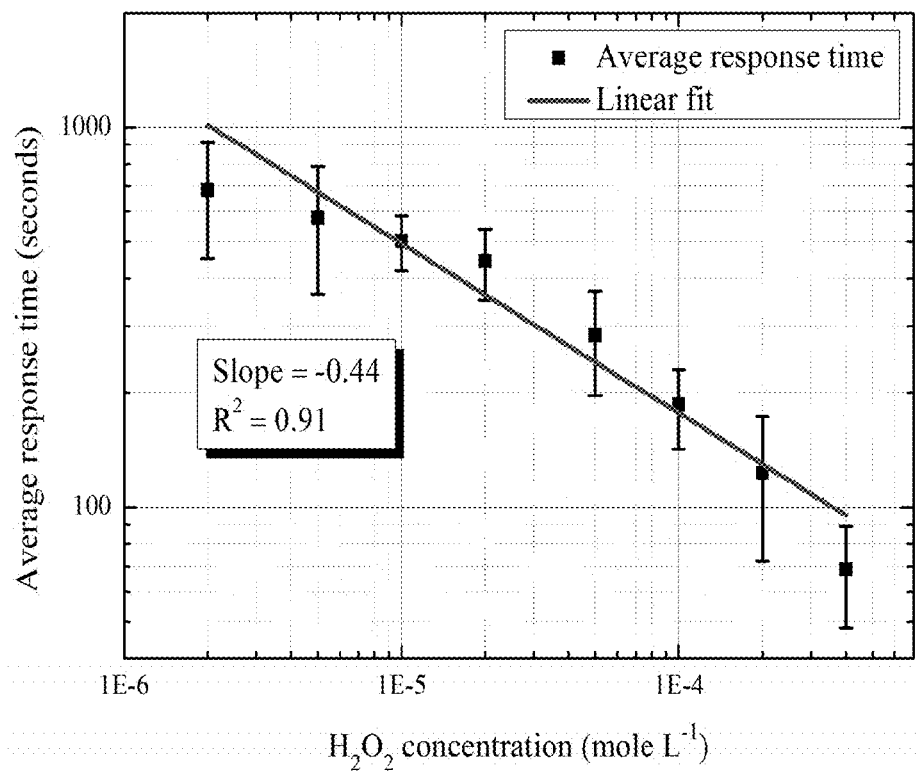
FIG. 10 is a graph of average response time (seconds) versus $H_2O_2$ concentration (mol/L) illustrating the average time response of a representative sensing device as a function of hydrogen peroxide concentration.

Various examples comprising multiple sensing tests were explored with the same sensing device to demonstrate the repeatability of the results obtained with the sensing device. As noted herein, the sequence of concentrations of the $H_2O_2$ solutions was different. FIG. 10 illustrates results obtained from these examples. The time response vs. concentration results for four embodiments using the same sensing device with different sequences of sensing methods are illustrated in FIG. 10. These sequences include two sets with random concentrations, one decreasing and then increasing the concentration, and one increasing and then decreasing the concentration. The error bars are the Estimated Standard Deviation (STDEV) for each concentration. The sensing device exhibits a linear behavior with slopes similar to those in the single test presented in FIG. 9.

Reproducibility

Figure 11A:
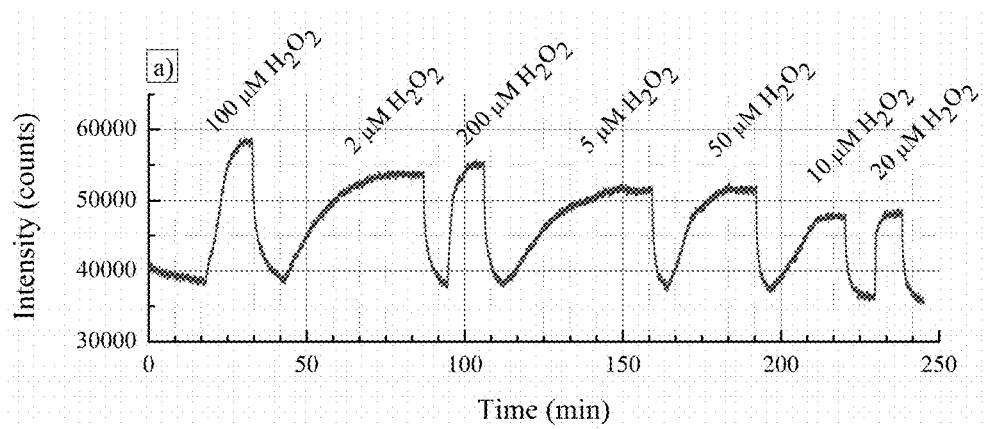
FIGS. 11A-11C are graphs of intensity (counts) versus time (minutes) illustrating the intensity response of three representative different sensing devices to immersion in solutions containing hydrogen peroxide.
Figure 11B:
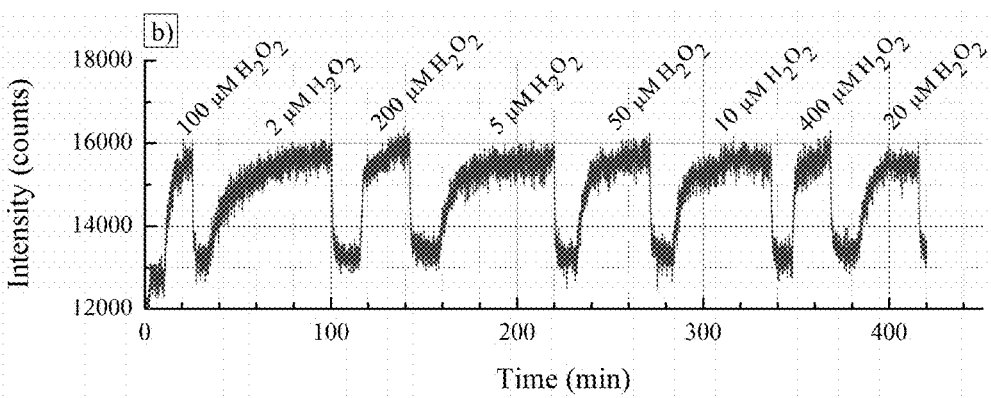
Figure 11C:
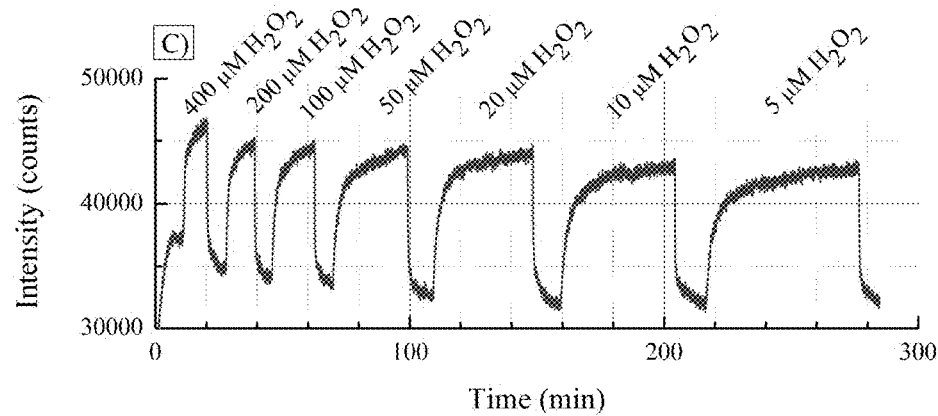

In this example, three sensing devices were prepared in the same manner at different times and multiple sensing methods were performed with each device. The intensity response of these sensing devices is illustrated in FIG. 11. The saturation intensities at PB and PW states are different for different sensing devices, but all devices exhibited the same behavior and the characteristic decrease in response time with higher $H_2O_2$ concentration.

As discussed herein, the intensity of the optical signals is related to the extent of reaction. In term of constant $H_2O_2$ concentration, the extent of reaction is related to the thickness and porosity of the PB/PW film. Also, each prepared optical fiber has its own initial intensity of reflectance, since the flat surface of the distal portion of optical fibers does not always have the same angle with the axis of the optical fiber. The offset of the signals from each sensing device is therefore likely caused by a combination of variation of the PB/PW film thicknesses, porosities, and the angle of flat surface of distal portion of optical fiber with the axis of optical fiber. The formation of the PB film is photoinduced with a light source placed outside the glass container where the reaction takes place. Although solution pH, concentration of reagent, and time and temperature of reaction are well controlled, the light intensity can potentially vary among all prepared sensing devices. This may have caused different thicknesses and microstructures for the deposited sensing films, and hence different reflected intensities from the distal portion of each of the optical fibers.

Figure 12:
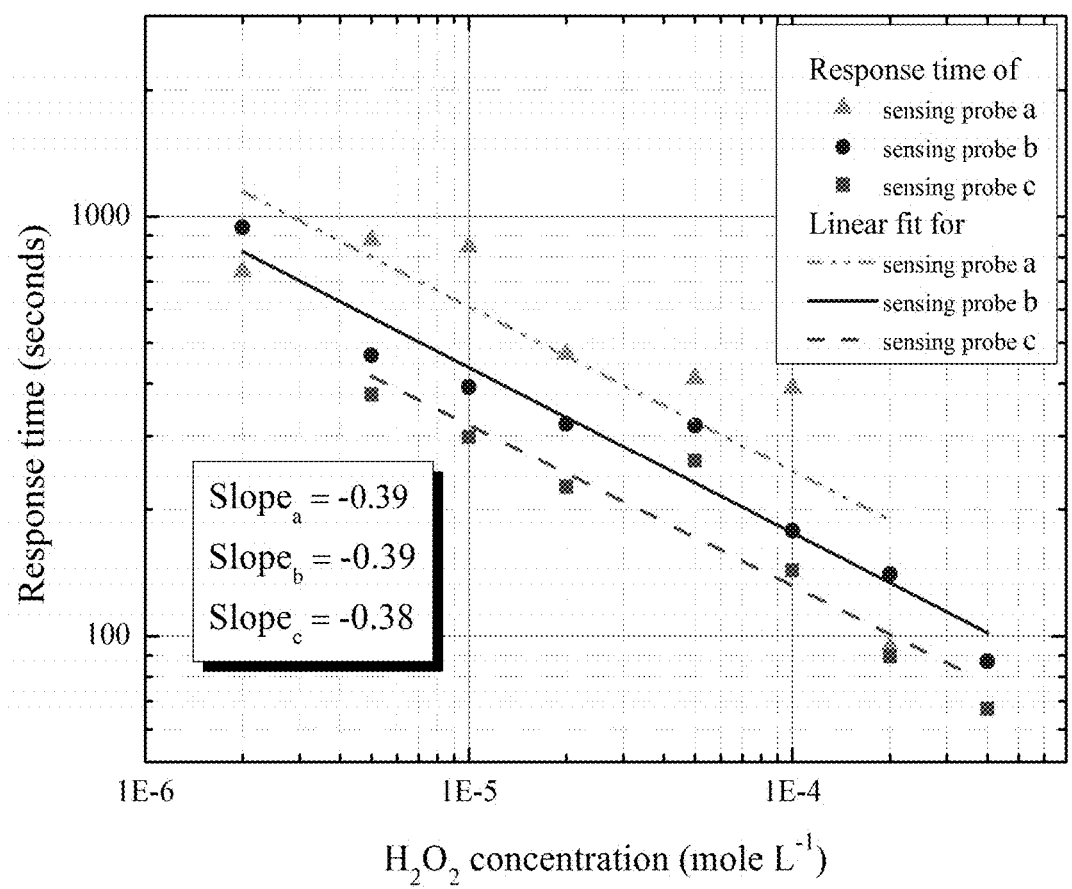
FIG. 12 is a graph of response time (seconds) versus $H_2O_2$ concentration (mol/L) illustrating the time response of three different representative sensing devices as a function of hydrogen peroxide concentration.

FIG. 12 depicts the time response vs. $H_2O_2$ concentration of the sensing devices, extracted from FIG. 11. The sensing behavior is similar for all three sensing devices. The slopes for the best linear fit on the time response of each sensing device are roughly the same. However, the intersect with the vertical axis changes. This particularity denotes that each sensor may require an initial calibration with known concentrations of $H_2O_2$ to determine its behavior prior to be exposed to an unknown amount of $H_2O_2$. The different vertical intersects of the sensing devices can be again attributed to the sensing film thickness or the film microstructure which affects the diffusion condition and leads to different diffusion time. However, the similarity observed in the slopes for the different sensing devices suggests that this parameter depends mainly on the nature of the deposited PB/PW film and that is independent of the film thickness and structure.

Durability

Figure 13A:
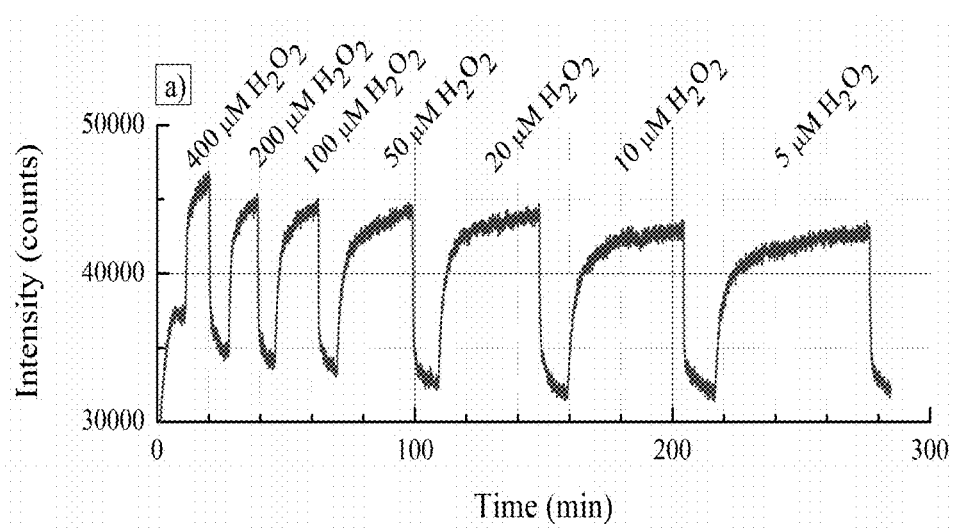
FIGS. 13A and 13B are graphs of intensity (counts) versus time (minutes) illustrating the intensity response of a representative sensing device to immersion in solutions containing hydrogen peroxide four (FIG. 13A) and seven months (FIG. 13B) after fabrication.
Figure 13B:
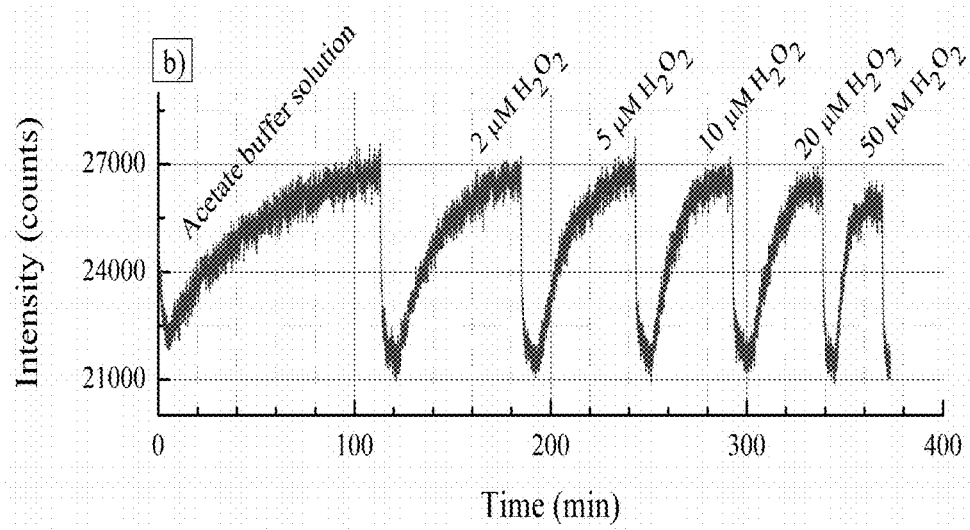

The durability of sensing device embodiments and the reliability in the measurements were evaluated by performing similar sensing methods four and seven months after fabrication. The intensity responses of the sensing device are illustrated in FIG. 13. The maximum intensity that the signal reached is slightly lower for the device tested in the seventh month. Since the device was subjected to multiple tests within the fourth and seventh months, the decrease may be due to alterations in the microstructure of the immobilized compound. In contrast, conventional sensors do not exhibit similar durability in such a time range due to leaching, which can be so extensive to as to cause the sensor to become inoperable over time. Hence to ensure accurate measurements in $H_2O_2$ concentration, periodic recalibrations may be used in practice.

Figure 14:
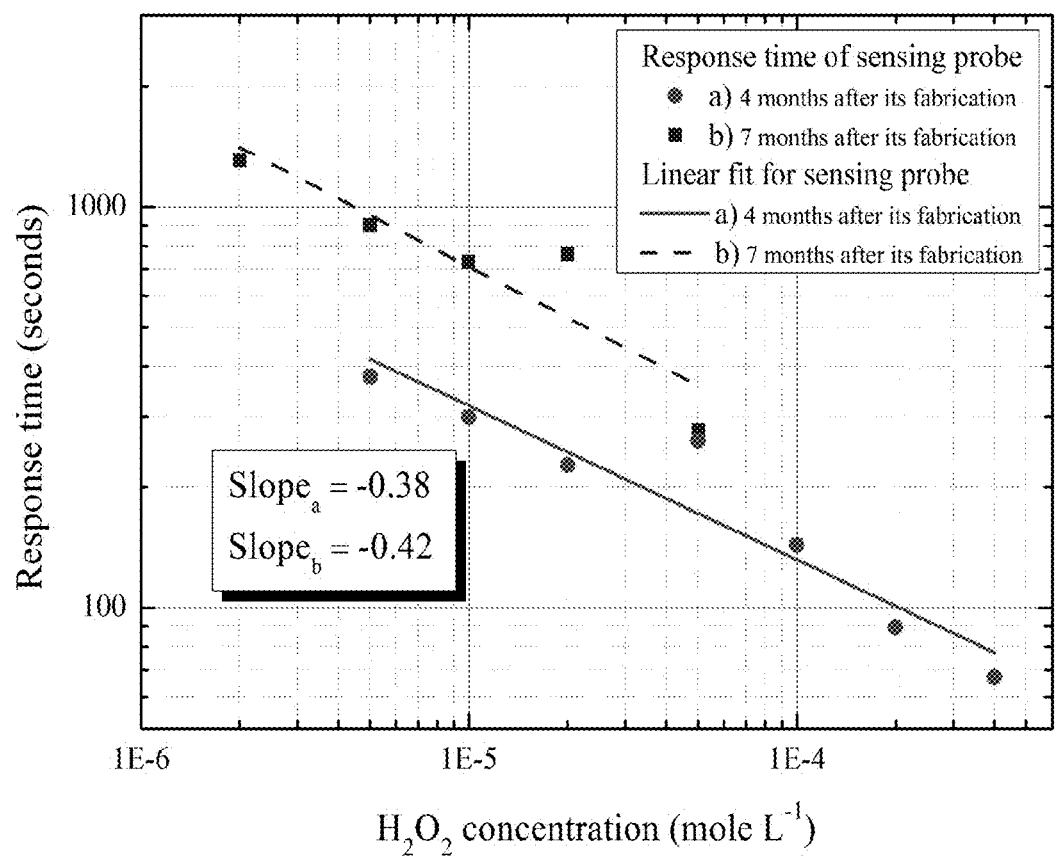
FIG. 14 is a graph of response time (seconds) versus $H_2O_2$ concentration (mol/L) illustrating the time response of a representative sensing device as a function of hydrogen peroxide concentration four (circles) and seven months (squares) after fabrication.

FIG. 14 depicts the time response of the experiments remains linear with the sensing device for the fourth and seventh months. The response and the slopes are essentially the same for both data sets. However, the vertical intersect is shifted towards slower response times in the more aged device. Slower diffusion times could again be due to possible alterations in the microstructure of the deposited film that difficult the access of the oxidant to the reaction sites. The sensing device was found to remain nonetheless functional for an extended period of time and multiple experiments. The results presented herein show that embodiments of the disclosed sensing device can be used to detect $H_2O_2$ as well as quantify the concentration of $H_2O_2$. The results also illustrate that the fabrication methods disclosed herein can facilitate mass production of the sensing devices.

In view of the many possible embodiments to which the principles of the present disclosure may be applied, it should be recognized that the illustrated embodiments are only preferred examples of the present disclosure and should not be taken as limiting the scope of the disclosure. Rather, the scope of the present disclosure is defined by the following claims.

We claim:

1. A method for making a sensing device, comprising:
providing a light guide having a distal portion terminating at a light guide tip and a proximal portion;
immersing the light guide tip of the distal portion in a single-source precursor and an acidic medium to initiate chemical deposition of a sensing component consisting of a layer of pure Prussian blue on the light guide tip; and annealing the light guide tip at a temperature ranging from 80° C. to 120° C. after the layer of pure Prussian blue is chemically deposited on the light guide tip using light having a wavelength ranging from 380 nm to 800 nm.

2. The method according to claim 1, further comprising preparing the distal portion of the light guide by cleaving an end of the distal portion to form the light guide tip and cleaning the light guide tip with a solvent before chemically depositing the layer of pure Prussian blue.

3. The method according to claim 1, wherein the pure Prussian blue is nanostructured pure Prussian blue.

4. The method according to claim 1, wherein the single-source precursor comprises $K_3Fe(CN)_6$.

5. The method according to claim 1, wherein the acidic medium is hydrochloric acid.

6. The method according to claim 1, wherein the pure Prussian blue is chemically deposited on the light guide tip of the distal portion at a temperature ranging from 19° C. to 50° C.

7. The method according to claim 6, wherein the temperature ranges from 35° C. to 45° C.

8. The method according to claim 1, wherein the light guide tip is annealed at 100° C.

* * * * *